United States Patent [19]

Damon, II et al.

[11] 4,329,349
[45] May 11, 1982

[54] 6-$C_{1-4}$ALKYL-7-PHENYL OR SUBSTITUTED PHENYL-1,6-NAPHTHYRIDINE-5(6H)-ONES

[75] Inventors: Robert E. Damon, II, Randolph; Jeffrey Nadelson, Denville, both of N.J.

[73] Assignee: Sandoz, Inc., East Hanover, N.J.

[21] Appl. No.: 171,824

[22] Filed: Jul. 24, 1980

Related U.S. Application Data

[63] Continuation-in-part of Ser. No. 60,729, Jul. 25, 1979, abandoned.

[51] Int. Cl.³ .................. C07D 471/04; A61K 31/435
[52] U.S. Cl. .................................... 424/256; 546/122; 546/316
[58] Field of Search ...................... 546/123, 316, 122; 424/256

[56] References Cited

U.S. PATENT DOCUMENTS 4,103,257  7/1978  Hammond et al. ................ 331/94.5
4,154,837  5/1979  Heider et al. ..................... 424/258

OTHER PUBLICATIONS

Ames et al., J. Chem. Soc. Perkin I 1972, 705-710.
Brown et al., J. Org. Chem. 40, 660-661 (1975).
Hawes et al., J. Hetero. Chem. 11, 151-155 (1974).
Paudler et al., J. Hetero. Chem. 5, 561-564 (1968).
Pokorny et al., J. Hetero. Chem. 9, 1151-1153 (1972).
Takeuchi et al., Chem. Pharm. Bull. 24, 1813-1821 (1976).
Merck Index, 9th Ed., pp. 5818-5819, Merck and Co., Rahway, N.J. (1976).
Wibberley, J. Chem. Soc. 1962, pp. 4528-4531.

Primary Examiner—Alan L. Rotman
Attorney, Agent, or Firm—Gerald D. Sharkin; Richard E. Vila; Melvyn M. Kassenoff

[57] ABSTRACT

Compounds of the formula

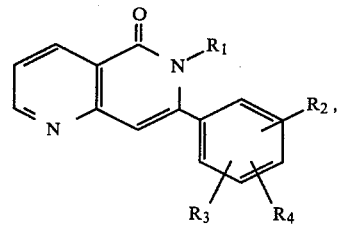

and pharmaceutically acceptable acid addition salts thereof,
wherein
$R_1$ is $C_{1-4}$alkyl,
$R_2$ is hydrogen, $C_{1-4}$alkyl, $C_{1-4}$alkoxy, halo, trifluoromethyl, $C_{1-4}$alkylthio or $-NR_5R_6$, wherein each of $R_5$ and $R_6$ is independently hydrogen or $C_{1-3}$alkyl,
$R_3$ is hydrogen, $C_{1-3}$alkyl, $C_{1-3}$alkoxy, halo or trifluoromethyl, and
$R_4$ is hydrogen, $C_{1-3}$alkyl, $C_{1-3}$alkoxy or halo,
their use as muscle relaxants and as anti-inflammatory agents, pharmaceutical compositions comprising them, processes for their synthesis and compounds of the formulae

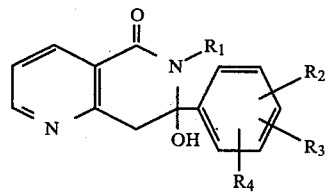

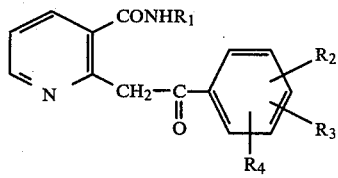

and

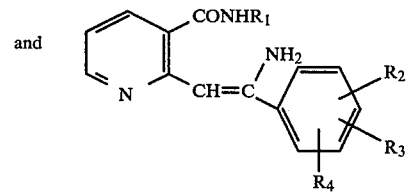

wherein $R_1$, $R_2$, $R_3$ and $R_4$ are as defined above, useful as intermediates in their synthesis.

26 Claims, No Drawings

6-$C_{1-4}$ALKYL-7-PHENYL OR SUBSTITUTED PHENYL-1,6-NAPHTHYRIDINE-5(6H)-ONES

This application is a continuation-in-part of application Ser. No. 60,729, filed July 25, 1979 and now abandoned.

This invention relates to compounds of the formula

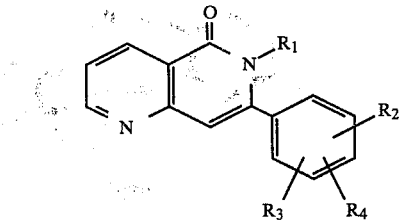

and pharmaceutically acceptable acid addition salts thereof,
wherein
$R_1$ is $C_{1-4}$alkyl,
$R_2$ is hydrogen, $C_{1-4}$alkyl, $C_{1-4}$alkoxy, halo, trifluoromethyl, $C_{1-4}$alkylthio or —$NR_5R_6$, wherein each of $R_5$ and $R_6$ is independently hydrogen or $C_{1-3}$alkyl,
$R_3$ is hydrogen, $C_{1-3}$alkyl, $C_{1-3}$alkoxy, halo or trifluoromethyl, and
$R_4$ is hydrogen, $C_{1-3}$alkyl, $C_{1-3}$alkoxy or halo,
their use as muscle relaxants and as anti-inflammatory agents, pharmaceutical compositions comprising them, processes for their synthesis and intermediates useful in their synthesis.

$R_1$ is preferably $C_{1-3}$alkyl, more preferably $C_{1-2}$alkyl and most preferably methyl.

$R_2$ is preferably hydrogen, $C_{1-3}$alkyl, $C_{1-2}$alkylthio, halo, trifluoromethyl or 2- or 3-dimethylamino, more preferably hydrogen, $C_{1-2}$alkyl, chloro, fluoro or 2- or 3-dimethylamino, even more preferably $C_{1-2}$alkyl, chloro, fluoro or 3-dimethylamino, still more preferably 2-$C_{1-2}$alkyl, 2-chloro, 2-fluoro or 3-dimethylamino and most preferably 2-methyl or 2-chloro.

$R_3$ is preferably hydrogen, $C_{1-3}$alkyl or halo, more preferably hydrogen, $C_{1-2}$alkyl, chloro or fluoro, still more preferably hydrogen or 6-fluoro and most preferably hydrogen $R_4$ is preferably hydrogen.

Each of $R_5$ and $R_6$ is preferably, independently, $C_{1-2}$alkyl, more preferably methyl.

Preferably, one of the ortho positions of the phenyl ring has a hydrogen atom or a fluoro substituent.

The free bases are preferred.

Each halo is independently fluoro, chloro or bromo, unless otherwise defined, preferably fluoro or chloro and more preferably chloro.

The preferred compounds of this application are the compounds of Formula I
wherein
$R_1$ is $C_{1-3}$alkyl,
$R_2$ is hydrogen, $C_{1-2}$alkyl, chloro, fluoro or 2- or 3-dimethylamino,
$R_3$ is hydrogen, $C_{1-2}$alkyl, chloro or fluoro, and
$R_4$ is hydrogen, with the proviso that at least one of the ortho positions of the phenyl ring has a hydrogen or fluoro atom,
and the pharmaceutically acceptable acid addition salts thereof, especially the free bases.

Even more preferred are the compounds of Formula I
wherein
$R_1$ is $C_{1-2}$alkyl, especially methyl,
$R_2$ is $C_{1-2}$alkyl, chloro, fluoro or 3-dimethylamino,
$R_3$ is hydrogen, and
$R_4$ is hydrogen,
and the pharmaceutically acceptable acid addition salts thereof, especially the free bases.

Still more preferred are the compounds of Formula I
wherein
$R_1$ is $C_{1-2}$alkyl, especially methyl,
$R_2$ is 2-$C_{1-2}$alkyl, 2-chloro, 2-fluoro or 3-dimethylamino,
$R_3$ is hydrogen, and
$R_4$ is hydrogen,
and the pharmaceutically acceptable acid addition salts thereof, especially the free bases.

The most preferred compounds of Formula I are those
wherein
$R_1$ is methyl,
$R_2$ is 2-chloro or 2-methyl,
$R_3$ is hydrogen, and
$R_4$ is hydrogen,
and the pharmaceutically acceptable acid addition salts thereof, especially the free bases.

Other groups of compounds of Formula I are those
wherein
$R_1$ is $C_{1-4}$alkyl,
$R_2$ is hydrogen, $C_{1-4}$alkyl, $C_{1-4}$alkoxy, halo, trifluoromethyl or —$NR_5R_6$, with the proviso that when $R_2$ is —$NR_5R_6$ it is in an ortho or meta position, wherein each of $R_5$ and $R_6$ is independently hydrogen or $C_{1-3}$alkyl,
$R_3$ is hydrogen, $C_{1-3}$alkyl, $C_{1-3}$alkoxy, halo or trifluoromethyl, and
$R_4$ is hydrogen, $C_{1-3}$alkyl, $C_{1-3}$alkoxy or halo,
and the pharmaceutically acceptable acid addition salts thereof, especially the free bases; those
wherein
$R_1$ is $C_{1-3}$alkyl,
$R_2$ is hydrogen, $C_{1-2}$alkyl, chloro or 3-dimethylamino,
$R_3$ is hydrogen, $C_{1-2}$alkyl or chloro, and
$R_4$ is hydrogen,
and the pharmaceutically acceptable acid addition salts thereof, especially the free bases; those
wherein
$R_1$ is $C_{1-2}$alkyl, especially methyl,
$R_2$ is $C_{1-2}$alkyl, chloro or 3-dimethylamino,
$R_3$ is hydrogen, and
$R_4$ is hydrogen,
and the pharmaceutically acceptable acid addition salts thereof, especially the free bases; those
wherein
$R_1$ is $C_{1-4}$alkyl,
$R_2$ is hydrogen, $C_{1-4}$alkyl, halo, trifluoromethyl, $C_{1-4}$alkylthio or —$NR_5R_6$, wherein each of $R_5$ and $R_6$ is independently hydrogen or $C_{1-3}$alkyl,
$R_3$ is hydrogen, $C_{1-3}$alkyl, halo or trifluoromethyl, and
$R_4$ is hydrogen, $C_{1-3}$alkyl or halo,
and the pharmaceutically acceptable acid addition salts thereof, especially the free bases; those
wherein
$R_1$ is $C_{1-4}$alkyl, particularly $C_{1-2}$alkyl, especially methyl, $R_2$ is hydrogen, $C_{1-4}$alkyl, halo, trifluoromethyl or $-NR_5R_6$, with the proviso that when $R_2$ is $-NR_5R_6$ it is in an ortho or meta position, wherein each of $R_5$ and $R_6$ is independently hydrogen or $C_{1-3}$alkyl, $R_3$ is hydrogen, $C_{1-3}$alkyl, halo or trifluoromethyl, and $R_4$ is hydrogen, $C_{1-3}$alkyl or halo, and the pharmaceutically acceptable acid addition salts thereof, especially the free bases; and those wherein $R_1$ is $C_{1-3}$alkyl, particularly $C_{1-2}$alkyl, especially methyl, $R_2$ is hydrogen, $C_{1-3}$alkyl, halo, trifluoromethyl or 2- or 3-dimethylamino, $R_3$ is hydrogen, $C_{1-3}$alkyl or halo, and $R_4$ is hydrogen, and the pharmaceutically acceptable acid addition salts thereof, especially the free bases.

All pharmaceutically acceptable acid addition salts of the compounds of Formula I (i.e., those salts which do not significantly increase the toxicity of the basic compound or otherwise adversely effect its pharmacological activity) are included within the scope of this invention. Included are salts with inorganic acids, e.g., the hydrochloride, hydrobromide, hydroiodide, phosphate (including hydrogen phosphates), metaphosphate, sulfate (including hydrogen sulfate) and perchlorate salts and salts with organic acids, e.g., the methanesulfonate, ethanesulfonate, benzenesulfonate and p-toluenesulfonate salts. However, the free bases are preferred.

The compounds of Formula I are synthesized by the following reaction sequence:

Reaction A

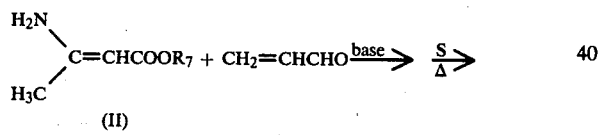

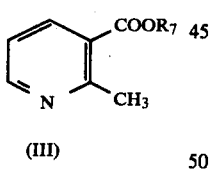

Reaction B

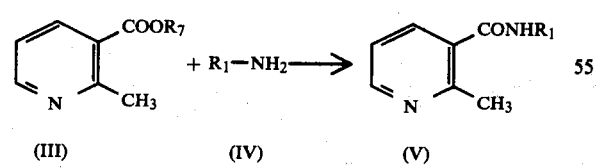

Reaction C

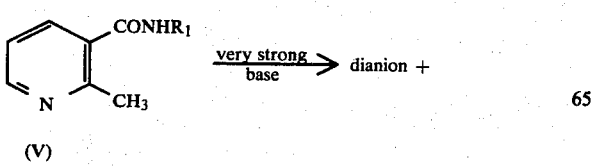

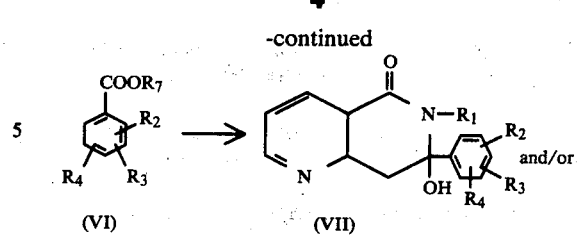

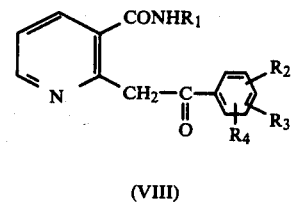

Reaction D

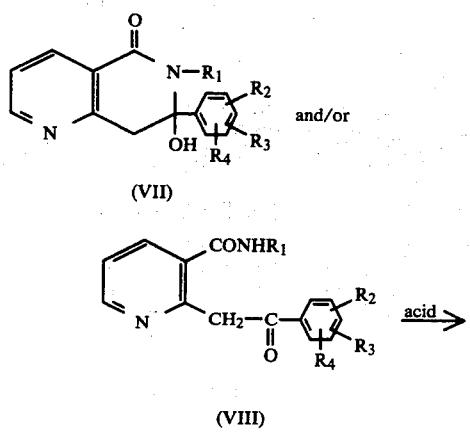

Alternatively, the compounds of Formula VIII can be prepared from the compounds of Formula V by the following reaction sequence:

Reaction C'

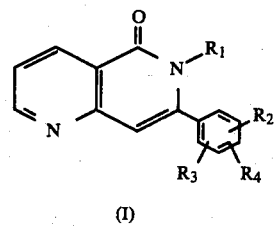

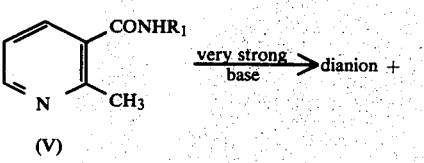

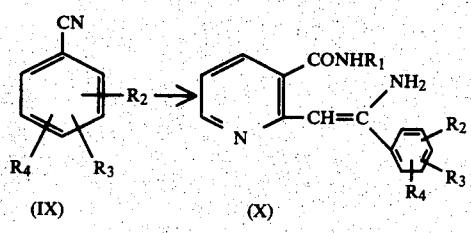

Reaction C"

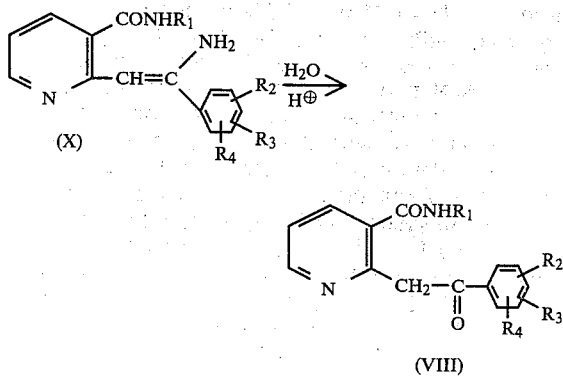

In formulae II-X
each $R_7$ is independently n-$C_{1-3}$alkyl, preferably $C_{1-2}$alkyl and most preferably ethyl, and
$R_1$, $R_2$, $R_3$ and $R_4$ are as defined above.

Reaction A is a two step reaction. In the first step of Reaction A an n-$C_{1-3}$alkyl 3-aminocrotonate of Formula II is reacted with acrolein to form an unisolated intermediate. The n-$C_{1-3}$alkyl 3-aminocrotonates of Formula II are commercially available or preparable by known methods. While the configuration about the double bond is not known, it is the more stable form (in which the amino and ethoxycarbonyl groups are believed to be cis to each other), which in the case of ethyl 3-aminocrotonate has a melting point of 33°–35° C., that is utilized. The first step of Reaction A is conveniently run by slowly adding acrolein, e.g., over a two hour period, to a mixture of an n-$C_{1-3}$alkyl 3-aminocrotonate and a secondary amine base, preferably a cyclic base such as piperidine or pyrrolidine, especially the former, in an inert organic solvent having a boiling point of at least 70° C., preferably 80°–100° C., e.g., isopropanol, and heating the resulting reaction mixture at a temperature of about 70° C. to the reflux temperature. Since the reaction time is, as is known to those in the art, inversely related to the reaction temperature, a precise reaction time cannot be given. However, a reaction time of 2–5 hours, preferably about 3½ hours, is generally utilized. While the molar ratio of acrolein to the n-$C_{1-3}$alkyl 3-aminocrotonate can theoretically be as low as 1:1, an excess of acrolein is employed; the molar ratio is preferably 1.2–2:1, more preferably 1.4–1.6:1. Only a small amount of the secondary amine base is needed, the molar ratio of secondary amine base to acrolein conveniently being 0.01–0.2:1. In the second step of Reaction A, the crude intermediate obtained from the first step by removing the solvent is dehydrogenated with sulfur. This step is conveniently run by simply adding a large excess of sulfur to the crude intermediate and heating at 100°–135° C. for 3–6 hours, conveniently at 100° C. for 2 hours and then at 125° C. for a further 1½ hours. While, as set forth above, a large molar excess of sulfur is employed, the molar ratio of sulfur to n-$C_{1-3}$alkyl 3-aminocrotonate is conveniently 2–10:1, preferably 3–6:1.

In Reaction B, the n-$C_{1-3}$alkyl 2-methylnicotinate of Formula III is amidated with a $C_{1-4}$alkylamine of Formula IV to obtain a 2-methylnicotinic acid N-$C_{1-4}$-alkylamide of Formula V. Conventional reaction conditions are utilized. The reaction temperature is conveniently 25°–75° C., 45°–55° C. being particularly convenient. While it is impossible to give a precise reaction time since the reaction time is inversely related to the reaction temperature, i.e., the higher the reaction temperature the shorter the reaction time, and, furthermore, depends upon the precise reactants utilized, a reaction time of 2–8 hours is typical, with a reaction time of 3–5 hours being particularly preferred especially when the reaction temperature is 45°–55° C. and an n-$C_{1-4}$alkylamine is utilized. The molar ratio of the $C_{1-4}$alkylamine of Formula IV to the n-$C_{1-3}$alkyl 2-methylnicotinate of Formula III can be as low as 1:1; however, a large excess of the former, e.g. 2–15 mols of the former per mol of the latter, is usually used, a molar ratio of 5–10:1 being typical. The reaction is run in an inert solvent such as water, tetrahydrofuran or a $C_{1-4}$alkanol, water being particularly convenient especially when methylamine is utilized.

Reaction C is a two step reaction. In the initial step, a 2-methylnicotinic acid N-$C_{1-4}$alkylamide of Formula V is reacted with a very strong, preferably bulky, base to generate the corresponding dianion. The reaction is run by slowly combining a solution of a very strong, preferably bulky, base such as a lithium di-($C_{1-4}$alkyl)amide, dicyclohexylamide or N-$C_{1-4}$alkyl-N-cyclohexylamide, e.g., lithium diethylamide, lithium dicyclohexylamide, lithium N-cyclohexyl-N-isopropylamide and, especially, lithium diisopropylamide, with a solution of the 2-methylnicotinic acid N-$C_{1-4}$alkylamide of Formula V under an inert atmosphere, e.g., under nitrogen, the solvent being an inert dry aprotic organic solvent such as toluene, 1,2-dimethoxyethane, diglyme and tetrahydrofuran, especially tetrahydrofuran. Two equivalents of the very strong base per mol of the compound of Formula V are employed to generate the dianion. A reaction temperature of −60°–25° C., preferably −30°–−5° C., most preferably −20° C., and a reaction time of 1–5 hours, preferably 1–3 hours, most preferably 2 hours, are employed. While a solution of either reactant may be slowly added to a solution of the other, it is usually the solution of the 2-methylnicotinic acid N-$C_{1-4}$alkylamide of Formula V that is slowly added to the solution of the base.

In the second step of Reaction C, a solution of an n-$C_{1-3}$alkyl benzoate of Formula VI in an inert dry aprotic organic solvent, preferably the same solvent utilized in the initial step, is slowly added to the solution of the dianion obtained from the initial step with stirring under an inert atmosphere, preferably nitrogen. Approximately equimolar amounts of the n-$C_{1-3}$alkyl benzoate of Formula VI and the dianion (assuming 100% conversion of the 2-methylnicotinic acid N-$C_{1-4}$alkylamide of Formula V to the dianion) are utilized; however, a small molar excess, e.g., 5%, of the n-$C_{1-3}$-alkyl benzoate of Formula VI may be used. Following the addition, stirring is continued at −60°–25° C., preferably −30°–−5° C., most preferably −20° C. While a precise reaction time cannot be given, a reaction time of 1–5 hours is generally used, with a reaction time of 1–3 hours being preferred and a reaction time of 2 hours being particularly preferred especially when the reaction temperature is −20° C. The n-$C_{1-3}$-alkyl benzoates of Formula VI are known or synthesizable by known methods.

The product of Reaction C, i.e., the hydroxylactam of Formula VII or the ketone of Formula VIII or the mixture of a hydroxylactam of Formula VII and the corresponding ketone of Formula VIII can be isolated conventionally and purified by conventional chromatography and/or recrystallization. However, it is unnecessary to do so since the crude product may be utilized in Reaction D. Which product(s) is (are) obtained depends upon the starting material, etc.

Reaction C', like Reaction C, is a two step reaction. The first step is identical to the first step of Reaction C, i.e., a 2-methylnicotinic acid N-methylamide of Formula V is converted to its dianion by reaction with a very strong, preferably bulky, base, the reaction conditions being identical to those of the first step of Reaction C. In the second step of Reaction C', the dianion generated in the first step is reacted with a benzonitrile of Formula IX to form an enamine of Formula X; the reaction conditions utilized are identical to those utilized in the second step of Reaction C. The configuration about the double bond of the enamines of Formula X has not been determined. However, it is believed that the amino group and the hydrogen atom are trans to each other. The benzonitriles of Formula IX are known or synthesizable by known methods.

In Reaction C'', the enamine of Formula X is hydrolyzed with aqueous acid to form the corresponding ketone of Formula VIII. While the reaction conditions employed are not critical, a weak aqueous acid is generally utilized to obtain the ketone of Formula VIII since the use of a strong acid will at least partially convert the ketone of Formula VIII to the desired naphthyridone of Formula I. It is convenient to employ aqueous acetic acid in a mixture of tetrahydrofuran and ethanol, although any inert solvent may be used. The reaction temperature is conveniently 25°–75° C., a temperature of 40° C. being particularly convenient. While the reaction time is inversely related to the reaction temperature, a reaction time of ½–8 hours, preferably 1–5 hours, generally gives good results.

In Reaction D, the product of Reaction C or that of Reaction C'', i.e., the crude or purified hydroxylactam of Formula VII or ketone of Formula VIII or a mixture thereof, is treated with a strong acid to obtain the corresponding naphthyridone compound of Formula I. Any strong organic or mineral acid can be employed, e.g., trifluoromethanesulfonic acid, trifluoroacetic acid, p-toluenesulfonic acid, methanesulfonic acid, sulfuric acid, perchloric acid and hydrochloric acid, hydrochloric and trifluoromethanesulfonic acids being among the preferred acids. Among the preferred reaction solvents are $C_{1-4}$alkanols such as methanol and ethanol, tetrahydrofuran, methylene chloride and chloroform; however, any inert organic solvent in which the compound(s) of Formula VII and/or Formula VIII is (are) at least slightly soluble may be employed. The use of hydrogen chloride in ethanol is particularly convenient. A reaction temperature of 0° C. to the reflux temperature of the reaction mixture, preferably not in excess of 100° C., may be employed, e.g., 50° C. to the reflux temperature of the mixture, the preferred reaction temperature being 70°–80° C. While the reaction time is inversely related to the reaction temperature, a reaction time of 5–30 minutes is generally suitable when the reaction temperature is at least 50° C. with a reaction time of 5–15 minutes being particularly suitable when the reaction temperature is 70°–80° C. A reaction time of 1–6 hours is generally suitable when the reaction temperature is 0°–40° C. The compound of Formula I is isolated from the reaction mixture conventionally and purified by conventional column chromatography and/or recrystallization.

The compounds of Formula I are generally obtained and utilized in free base form. However, they can be converted into pharmaceutically acceptable (or other) acid addition salt form by conventional means, e.g., by treatment with acid. Likewise, any acid addition salt can be converted to the corresponding free base by conventional means, e.g., by treatment with sodium hydroxide. Hence, any acid addition salt that is not suitable for pharmaceutical use may be converted by conventional means into a free base or pharmaceutically acceptable acid addition salt that is suitable for such use.

The hydroxylactams of Formula VII, the ketones of Formula VIII and the enamines of Formula X are also within the scope of this invention. The preferred significances of $R_1$, $R_2$, $R_3$ and $R_4$ of the compounds of Formulae VII, VIII and X are identical to those given for the compounds of Formula I and the preferred, more preferred and other groups of compounds of Formulae VII, VIII and X identically correspond to those of the compounds of Formula I.

The compounds of Formula I and the pharmaceutically acceptable acid addition salts thereof are useful for the treatment of inflammation in animals (e.g., mammals) as indicated by Test E and, with the exception of those wherein $R_2$ is 4-$NR_5R_6$ and $R_3$ and $R_4$ are hydrogen, as muscle relaxants in animals (e.g., mammals) as indicated by Tests A, B, C and D. The preferred compounds of Formula I and pharmaceutically acceptable acid addition salts set forth above are those that are preferred for muscle relaxation.

Test A (Rotarod Test): A modification of the rotarod method of Dunham et al., J. Am. Pharm. Assoc. 46, 208 (1957), is used. Groups of 5 male Royal Hart mice weighing 20–25 g. are trained to ride a rod revolving at 15 r.p.m. covered with corrugated paper for 60–90 seconds. Ability of the mice to remain on the rod is tested again at 30 minutes and 60 minutes after intraperitoneal or oral administration of the drug (the compound of Formula I in free base or pharmaceutically acceptable acid addition salt form) at a dose of 20–400 mg./kg. body weight or saline. Rotarod times for control and treated groups are compared to determine the percent change. The $ED_{50}$ is the dose of the drug which decreases the rotarod time by 50% or is calculated by interpolation.

Test B (Gross Spinal Reflex): Male cats weighing 2.5–3.0 kg. are utilized to study the effects of drugs on the mono (patellar)—and poly (flexor)—synaptic gross spinal reflexes. A Grass Model 7 polygraph with two ft. 03 force displacement transducers and two low level D.C. pre-amplifiers is utilized to measure the flexor and patellar responses.

Anesthesia is induced with ether, followed by an i.v. injection of alpha chloralose dissolved in warm distilled water at a dose of 70 mg./kg. body weight. The trachea is cannulated following induction of anesthesia, the right saphenous vein is cannulated for use as the route of administration of the test material (drug), and the right carotid artery is cannulated for blood pressure recording.

A drill bit pin is inserted just behind the lateral epicondyle of the left femur. The left patellar tendon is wired to a solenoid patellar hammer that will trigger a patellar reflex every 10 seconds. Contraction of the left leg is measured via a force displacement transducer.

A drill bit pin is inserted just behind the lateral epicondyle of the right femur and above the lateral malleolus of the right tibia. The right tibialis anticus tendon is freed from its insertion on the anterior tuberosity and attached with silk suture to the force displacement transducer. The right sciatic nerve is exposed and all of the small nerves branching off the sciatic nerve to the surrounding muscles are cut. The popliteal nerve is isolated, ligated and crushed at its distal end. A bipolar electrode is applied to the proximal (center) end of the popliteal nerve and stimulated (using a S4 Grass stimulator) to produce the flexor (polysynaptic) response. The perineal nerve is carefully kept intact and the entire preparation is immersed in mineral oil.

A series of control responses is recorded prior to administration of the drug (compound of Formula I in free base or pharmaceutically acceptable acid addition salt form). The drug is then administered i.v. through the right saphenous vein in progressively accumulating doses (raised logarithmically), the total dose being 0.5–50 mg./kg. The $ED_{50}$ is the actual dose that reduces the response by 50% or is extrapolated from the actual data.

Test C (Modified Gross Spinal Reflex): This test is identical to Test B except that no alpha chloralose is administered. The spinal cord is carefully cut at C-1 while the cat is under ether (encephale isole); the cat is then put on a respiration pump.

Test D (Linguomandibular Reflex (LMR)): The linguomandibular reflex is a polysynaptic reflex involving interneurons within the brain stem. Inhibition of the linguomandibular reflex has been correlated with central muscle relaxant activity. See Bhargava et al., Brit. J. Pharmacol. 25, 74–80 (1965).

Male cats weighing 2.0–3.0 kg. are utilized to study the effect of a drug on the linguomandibular reflex. Each cat is anesthetized by an intraperitoneal injection of 70 mg./kg. of alpha chloralose. Cannulae are placed in the trachea, the right external jugular vein for use as the route of administration of the test drug and the left carotid artery for monitoring blood pressure.

The head of the cat is rigidly fixed in a Kopf stereotaxic u-frame assembly allowing the lower jaw (mandible) to move freely. The movement of the lower jaw is recorded through a system of surgical thread, pulleys and a ft. 03 force displacement transducer which in turn is connected to a Grass Model 7 polygraph for recording. In all experiments a resting baseline tension of 900 mg. is maintained on the mandible.

To elicit the jaw-opening linguomandibular reflex, two needle electrodes are placed in the root of the tongue and stimulated with a Grass S4 stimulator. Stimulus parameters are: 2.5–9 volts, 100 msec. duration and a frequency of 6/minute.

After consistent linguomandibular responses are obtained, the test drug (compound of Formula I in free base or pharmaceutically acceptable acid addition salt form) is administered intravenously at a dose of 2–50 mg./kg. body weight and its effect is recorded. The $ED_{50}$ is the actual dose that reduces the response by 50% or is calculated by extrapolation from the actual data.

Test E (Acute Carrageenan-Induced Edema): Rats are orally dosed (10–200 mg./kg. body weight) with the test drug (compound of Formula I in free base or pharmaceutically acceptable acid addition salt form) one hour prior to administration of carrageenan; edema is measured three hours subsequent to the carrageenan administration. See Winter, Proc. Soc. Exp. Biol. 111, 544 (1962).

The compounds of Formula I and their pharmaceutically acceptable acid addition salts may be formulated into conventional pharmaceutical compositions and administered by conventional modes of administration for muscle relaxants and anti-inflammatory agents. The compounds of each subgroup set forth in the specification and/or claims may be formulated into conventional pharmaceutical compositions.

The compounds of Formula I and their pharmaceutically acceptable acid addition salts may be combined with pharmaceutically acceptable carriers and other conventional pharmaceutical adjuvants and administered orally in the form of tablets, dispersible powders, granules, capsules, elixirs, suspensions and the like or parenterally in the form of a sterile injectable solution or suspension. The compositions may be prepared by conventional means and may contain one or more conventional adjuvants. The compounds of Formula I and their pharmaceutically acceptable acid addition salts may be micronized prior to administration.

The preferred pharmaceutical compositions from the stand-point of ease of preparation and administration are solid compositions, particularly tablets and hard-filled capsules.

The muscle relaxant effective dose of each compound of Formula I and the pharmaceutically acceptable acid addition salts thereof (other than those wherein $R_2$ is 4-$NR_5R_6$ and $R_3$ and $R_4$ are hydrogen) varies depending upon the particular compound employed, the host, the severity of the condition being treated and the mode of administration. However, in general, satisfactory results are obtained when the compound is administered orally at a daily dosage of 0.1–100 mg./kg. body weight, typically given in divided doses two to four times per day. For most larger mammals, the total daily oral dosage is 1–1000 mg./day, preferably 10–1000 mg./day, given in divided doses two to four times per day. For administration by injection, a dosage somewhat lower than would be used for oral administration of the same compound to the same host having the same condition is usually employed. However, the above dosages are also typically used for i.v. administration.

The anti-inflammatory effective dose of the compounds of Formula I and the pharmaceutically acceptable acid addition salts thereof is substantially the same as the muscle relaxant effective dose. Hence, the dosages set forth in the preceding paragraph are also effective for the treatment of inflammation.

A typical dosage unit for oral administration may contain 0.5 to 500 mg. of a compound of Formula I or a pharmaceutically acceptable acid addition salt thereof. Preferred dosage units contain 10 to 100 mg., especially 25 to 75 mg., of a compound of Formula I or a pharmaceutically acceptable acid addition salt thereof.

Representative formulations prepared by conventional techniques for encapsulation in a hard gelatin capsule are:

| | | |
|---|---|---|
| A. | Compound of Formula I in free base or pharmaceutically acceptable acid addition salt form, e.g., the compound of Example 4 | 25 mg. |
| | Lactose (spray-dried) | 50 mg. |
| B. | Compound of Formula I in free base or pharmaceutically acceptable acid addition salt form, e.g., the compound of Example 6 | 100 mg. |

-continued

| | |
|---|---|
| Powdered lactose | 100 mg. |

Representative formulations suitable for preparing tablets by conventional means are:

| | | |
|---|---|---|
| A. | Compound of Formula I in free base or pharmaceutically acceptable acid addition salt form, e.g., the compound of | |
| | Example 4 | 50 mg. |
| | Gum tragacanth | 10 mg. |
| | Powdered lactose | 152.5 mg. |
| | Corn starch | 25 mg. |
| | Talc. | 10 mg. |
| | Magnesium stearate | 2.5 mg. |
| B. | Compound of Formula I in free base or pharmaceutically acceptable acid addition salt form, e.g., the compound of | |
| | Example 6 | 50 mg. |
| | Gum tragacanth | 10 mg. |
| | Powdered lactose | 197.5 mg. |
| | Corn starch | 25 mg. |
| | Talc | 15 mg. |
| | Magnesium stearate | 2.5 mg. |

The following examples show representative compounds encompassed by this invention and their synthesis. However, it should be understood that they are for purposes of illustration only.

EXAMPLE 1

Ethyl 2-methylnicotinate

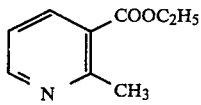 (XI)

To a mixture of 800 ml. of ethyl 3-aminocrotonate, 30 ml. of piperidine and 1.4 l. of isopropanol, stirred at 25°-30° C., 540 ml. of acrolein were added slowly over a 2 hour period with stirring. Upon completion of the addition of the acrolein, the reaction mixture was heated to reflux and refluxed for 3½ hours. Then the reaction mixture was evaporated at reduced pressure to dryness. The residue was heated to 100° C. and 610 g. of sulfur were added thereto portionwise. The reaction mixture was then heated at 100° C. for 2 hours and at 125° C. for 1½ hours. The reaction mixture was allowed to cool to about room temperature and 1 l. of chloroform was added thereto. The reaction mixture was filtered through Celite and the filter cake was washed with additional chloroform. The combined chloroform filtrate and washings were extracted three times with 1 l. portions of 2 N. hydrochloric acid. The aqueous acidic layers were combined and, with cooling, were made basic with 2 N. sodium hydroxide solution. The obtained aqueous basic solution was extracted three times with 1 l. portions of chloroform. The chloroform extracts were combined, washed with saturated brine, dried over anhydrous sodium sulfate and evaporated at reduced pressure to obtain an oily residue which was distilled under high vacuum to obtain the pure product (350 g.), b.p. 73°-77° C./0.5 mm. Hg.

EXAMPLE 2

2-Methylnicotinic acid N-methylamide

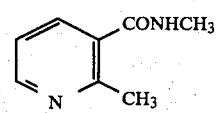 (XII)

200 g. (1.21 mol) of ethyl 2-methylnicotinate (Compound XI) and 1 l. of 40% aqueous methylamine were heated at 40° C. for 4 hours. The reaction mixture was stripped at reduced pressure to obtain the crude product (197.8 g.) as a thick oil which was distilled at 121°-133° C./0.18 mm. Hg. to give the product (175.8 g.), m.p. 69°-72° C.

EXAMPLE 3

7-(2'-Chlorophenyl)-7,8-dihydro-7-hydroxy-6-methyl-1,6-naphthyridine-5(6H)-one

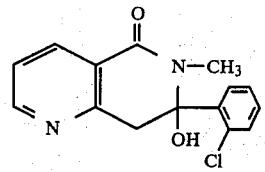 (XIII)

189 ml. of 1.6 M. n-butyl lithium (302.4 mmol.) in hexane were added to a solution of 42.3 ml. of diisopropylamine in 300 ml. of dry tetrahydrofuran stirred at $-5°--10°$ C. under nitrogen. To the resulting solution of lithium diisopropylamide, 21.5 g. (144 mmol.) of 2-methylnicotinic acid N-methylamide (Compound XII), dissolved in 150 ml. of dry tetrahydrofuran, were added slowly at $-20°--30°$ C. with stirring under nitrogen. The resulting reaction mixture was stirred under nitrogen at $-20°--30°$ C. for an additional 2 hours. Then, a solution of 26.8 g. (145 mmol.) of freshly distilled ethyl 2-chlorobenzoate in 150 ml. of dry tetrahydrofuran was slowly added to the reaction mixture stirred at $-20°--30°$ C. under nitrogen. Upon completion of the addition, stirring under nitrogen was maintained at the same temperature for an additional 1½ hours. The reaction mixture was then quenched with 250 ml. of concentrated sodium chloride solution and extracted three times with ethyl acetate. The obtained ethyl acetate extracts were combined, washed four times with water and once with saturated sodium chloride solution, dried over anhydrous sodium sulfate, filtered and evaporated at reduced pressure to obtain a thick oil (34.7 g.). The resulting oil was chromatographed on a silica gel column which was eluted with methylene chloride followed by 3% methanol/chloroform. The 3% methanol/chloroform eluant yielded the crude product (21.6 g.) which was crystallized from ether to yield the product (13.2 g.), m.p. 144°-146° C. A second crop (1.3 g.), m.p. 144°-146° C., was also obtained. The two crops were combined and recrystallized from toluene to obtain the product (12.5 g.), m.p. 143°-145° C. An analytical sample melted at 145° C. The mother liquors from the aforementioned second crop and the toluene crystallization were combined and evaporated at reduced pressure. The residue (5.4 g.) was dissolved in acetone and treated with 0.9 g.

of gaseous hydrogen chloride to obtain a crystalline material (1.8 g.).

EXAMPLE 4

7-(2'-Chlorophenyl)-6-methyl-1,6-naphthyridine-5(6H)-one

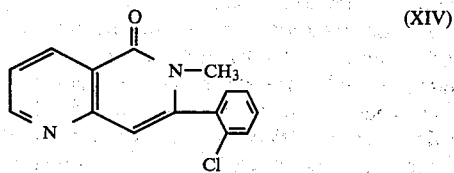
(XIV)

7.8 g. of Compound XIII (from Example 3) were suspended in 50 ml. of absolute ethanol and 1.1 g. of gaseous hydrogen chloride were bubbled in. The reaction mixture was then evaporated practically to dryness and the 1.8 g. of crystalline material from Example 3 and 100 ml. of absolute ethanol were added thereto. The resulting reaction mixture was refluxed for 5 minutes, cooled by addition of ice and water and made basic with sodium hydroxide solution. The basic solution was extracted with methylene chloride and the methylene chloride extract was dried over anhydrous sodium sulfate, filtered and evaporated at reduced pressure to obtain the crude product (8.1 g.) which was recrystallized from absolute ethanol to obtain the product (6.1 g.), m.p. 152°–153° C. A second crop (1.5 g.), m.p. 152°–153° C., was also obtained. An analytical sample melted at 153° C.

| Test A: | $ED_{50}$ = 49.3 mg./kg. i.p. |
|---|---|
|  | $ED_{50}$ = 39.1 mg./kg. p.o. |
| Test B: | $ED_{50}$ = 1.6 mg./kg. i.v. |
| Test D: | $ED_{50}$ = 4.6 mg./kg. i.v. |
| Test E: | $ED_{50}$ = 29 mg./kg. p.o. |

The compound of this example is an effective muscle relaxant when orally administered to a mammal in need of said treatment at a daily dosage of 75–200, e.g., 100, mg. in two to four divided doses, e.g., 25–50 mg. three or four times daily.

The compound of this example can be converted into its pharmaceutically acceptable acid addition salts by conventional means.

EXAMPLE 4A 7-(2'-Chlorophenyl)-6-methyl-1,6-naphthyridine-5(6H)-one.hydrochloride

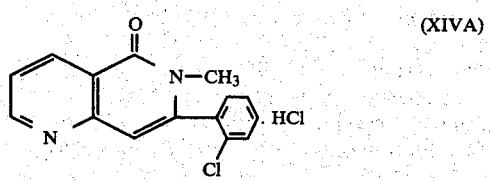
(XIVA)

358.3 mg. of Compound XIV were dissolved in absolute ethanol and gaseous hydrogen chloride was bubbled in for 1–2 minutes. A yellow precipitate formed. The reaction mixture was cooled and filtered to obtain the product as a yellow solid (341.3 mg.), m.p. 222°–229° C. (decomp.)

EXAMPLE 4B 7-(2'-Chlorophenyl)-6-methyl-1,6-naphthyridine-5(6H)-one.methanesulfonate

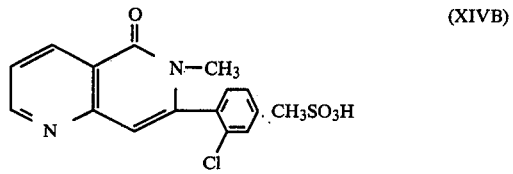
(XIVB)

66 µl. of methanesulfonic acid were added to a solution of 203.1 mg. (0.75 mmol.) of Compound XIV in ethanol. A yellow precipitate formed and was collected by filtration, m.p. 210°–220° C. (darkens and decomp.)

EXAMPLE 5

7,8-Dihydro-7-hydroxy-6-methyl-7-(2'-methylphenyl)-1,6-naphthyridine-5(6H)-one

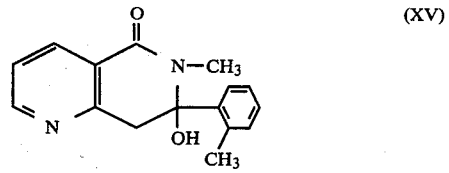
(XV)

109 ml. of 1.6 M. n-butyl lithium in hexane (174.4 mmol.) were added to a solution of 24.4 ml. of diisopropylamine in 200 ml. of dry tetrahydrofuran stirred at −10°–−30° C. under nitrogen. To the resulting solution of lithium diisopropylamide, 13.1 g. (87.3 mmol.) of 2-methylnicotinic acid N-methylamide (Compound XII), dissolved in 110 ml. of dry tetrahydrofuran, were added slowly at −30°–−20° C. with stirring under nitrogen. Stirring under nitrogen was continued for 2 hours at −30°–−20° C. Then 14.3 g. (87.2 mmol.) of freshly distilled ethyl 2-methylbenzoate dissolved in 60 ml. of dry tetrahydrofuran were slowly added at the same temperature and stirring under nitrogen was continued for a further 2 hours at the same temperature. The reaction mixture was then quenched with 150 ml. of concentrated sodium chloride solution and the reaction mixture was extracted three times with ethyl acetate. The ethyl acetate extracts were combined, washed six times with water, once with concentrated sodium chloride solution, dried over anhydrous sodium sulfate, filtered and evaporated at reduced pressure to obtain a crude material (20.4 g.). The crude material was dissolved in ethyl acetate and filtered through silica gel. Evaporation at reduced pressure yielded 16.3 g. of material which was separated into neutral and basic components by dissolving in toluene and cold 2 N. hydrochloric acid and extracting the toluene phase twice with cold 2 N. hydrochloric acid. The three aqueous phases were combined, made basic with sodium hydroxide solution and extracted twice with methylene chloride. The methylene chloride extracts were combined, dried over anhydrous sodium sulfate and evaporated at reduced pressure to obtain the basic component (8.7 g.), i.e., the crude hydroxylactam of Formula XV.

EXAMPLE 6

6-Methyl-7-(2'-methylphenyl)-1,6-naphthyridine-5-(6H)-one

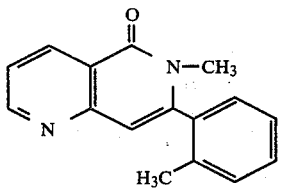

(XVI)

The crude hydroxylactam of Formula XV from Example 5 (8.7 g.) was dissolved in 100 ml. of ethanol and 1.2 g. of gaseous hydrogen chloride were added. The reaction mixture was refluxed for 10 min. and then cooled. Excess sodium hydroxide solution was then added and the resulting reaction mixture was extracted with methylene chloride. The methylene chloride extract was dried over anhydrous sodium sulfate, filtered and evaporated at reduced pressure to obtain a yellow oil (8.1 g.). Crystallization from ethanol yields 0.6 g. of crystals, m.p. 123°-124° C. The mother liquor was evaporated at reduced pressure to obtain 7.0 g. of crude product which was chromatographed on silica gel utilizing 5% ethyl acetate/hexane as the eluant. The early fractions, upon recrystallization from ethanol, yielded an additional 0.6 g. of crystals, m.p. 122.5°-124° C. The later fractions were combined and recrystallized from diethyl ether/pentane to obtain the desired product (2.20 g.), m.p. 104°-106° C. A second crop (0.66 g.), m.p. 102°-104° C., was also obtained. An analytical sample melted at 106° C.

| Test A: | $ED_{50}$ = 36.8 mg./kg. i.p. |
|---|---|
|  | $ED_{50}$ = 43.5 mg./kg. p.o. |

The compound of this example is an effective muscle relaxant when orally administered to an animal in need of said treatment at a daily dosage of 100 mg. in two to four divided doses.

The compound of this example can be converted into its pharmaceutically acceptable acid addition salts by conventional means.

EXAMPLE 7

2-(3'-Dimethylaminobenzoylmethyl)nicotinic acid N-methylamide

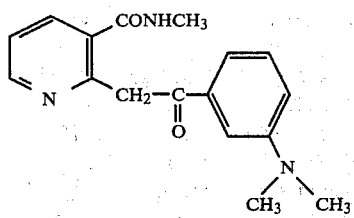

(XVII)

263 ml. of 1.6 M.n-butyl lithium in hexane (420 mmol.) were slowly added to a solution of 58.7 ml. (420 mmol.) of diisopropylamine in 200 ml. of dry tetrahydrofuran stirred at −10° C. under nitrogen. To the resulting solution of lithium diisopropylamide, a solution of 30 g. (200 mmol.) of 2-methylnicotinic acid N-methylamide (Compound XII) in 200 ml. of dry tetrahydrofuran was slowly added at −20°--30° C. The resulting red reaction mixture was stirred under nitrogen at −20°--30° C. for an additional two hours. Then, a solution of 38.6 g. (200 mmol.) of ethyl 3-dimethylaminobenzoate in 100 ml. of dry tetrahydrofuran was slowly added at −20°--30° C. with stirring under nitrogen. Stirring under nitrogen was continued for 1 hour at the same temperature. The reaction mixture was then quenched with 250 ml. of saturated sodium chloride solution and extracted three times with ethyl acetate. The ethyl acetate phases were combined, washed four times with water, once with saturated sodium chloride solution, dried over anhydrous sodium sulfate, filtered and evaporated at reduced pressure to a thick oil (55.6 g.) which was dissolved in a small amount of isopropanol and chromatographed on silica gel using 5% isopropanol/chloroform as the eluant. The last major fraction to be eluted (approx. 24 g.) was rechromatographed on silic gel using 2% isopropanol/chloroform as the eluant. The largest fraction contained the crude product (17.2 g.).

EXAMPLE 8

7-(3'-Dimethylaminophenyl)-6-methyl-1,6-naphthyridine-5(6H)-one

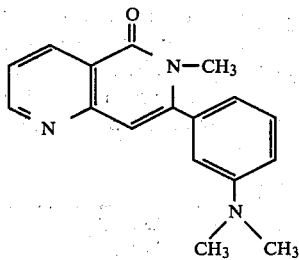

(XVIII)

The crude product of Example 7 (17.2 g.) was dissolved in ethanol and 4.3 g. of gaseous hydrogen chloride were bubbled in. The reaction mixture was heated for 5 minutes at 70° C. Two crops of a solid, 12.4 g., m.p. 197°-220° C. (dec.), and 1.9 g., m.p. 224°-226° (dec.), were obtained. The two crops were combined and recrystallized from ethanol to obtain 11.8 g., m.p. 221°-232° C. (dec.). The mother liquors from each of the crystallizations and recrystallizations were combined; two additional crops, 4.9 g. (total), m.p. 193°-216° C. (dec.), were obtained therefrom. 11.5 g. of the combined crystalline materials were dissolved in water, excess sodium hydroxide solution was added, and the basic solution was extracted with methylene chloride. The methylene chloride extract was dried over anhydrous sodium sulfate, filtered and evaporated at reduced pressure. The residue was chromatographed on silica gel using ethyl acetate as the eluant. The major fractions were combined and recrystallized from acetone/pentane, 7.6 g., m.p. 118°-120° C. An analytical sample had a melting point of 120° C. A second crop (2.4 g.), m.p. 117°-119° C., was also obtained.

| Test A: | $ED_{50}$ = | 141.2 mg./kg. i.p. |
|---|---|---|
|  | 47.3% | 200 mg./kg. p.o. |

The compound of this example can be converted into its pharmaceutically acceptable acid addition salts by conventional means; mono- and di- salts can be formed.

EXAMPLE 9

2-(4'-Chloro-β-aminostyryl)nicotinic acid N-methylamide

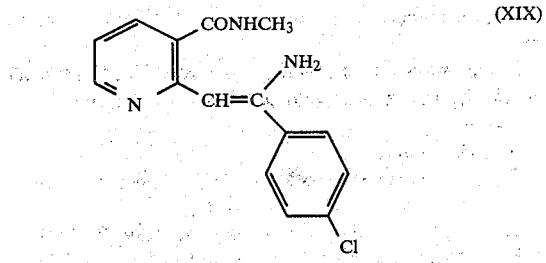

(XIX)

A solution of lithium diisopropylamide in dry tetrahydrofuran was prepared by slowly adding 292 ml. of 1.6 M.n-butyl lithium in hexane (467.2 mmol.) to a solution of 70 ml. of diisopropylamine in 400 ml. of dry tetrahydrofuran stirred at −20° C. under nitrogen. A solution of 35 g. (233.3 mmol.) of 2-methylnicotinic acid N-methylamide (Compound XII) in 400 ml. of dry tetrahydrofuran was slowly added, over a 30 min. period, to the lithium diisopropylamide solution stirred under nitrogen at −20° C. Stirring under nitrogen was continued at the same temperature for an additional 1½ hours. Then, a solution of 32.1 g. (233.4 mmol.) of 4-chlorobenzonitrile in dry tetrahydrofuran was slowly added. Stirring under nitrogen at −20° C. was continued for an additional 1½ hours. The reaction mixture was then warmed to room temperature over a 30 minute period and 500 ml. of water were added. The organic phase was washed with 500 ml. of saturated sodium chloride solution and the aqueous phase was extracted four times with 100 ml. portions of methylene chloride. The washed organic phase and the four methylene chloride extracts were combined, treated with charcoal, dried over anhydrous magnesium sulfate and concentrated at reduced pressure to the crude product which was recrystallized from diethyl ether/methylene chloride to give a yellow solid which was recrystallized again from diethyl ether/methylene chloride to give 25.8 g. of the product, m.p. 140°–145° C.

EXAMPLE 10

2-(4'-Chlorobenzoylmethyl)nicotinic acid N-methylamide

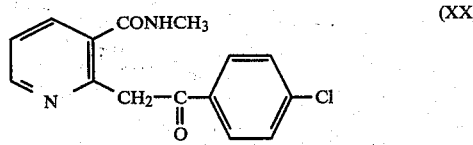

(XX)

22 g. (76.5 mmol.) of 2-(4'-chloro-β-aminostyryl)-nicotinic acid N-methylamide (Compound XIX) were dissolved in 80 ml. of tetrahydrofuran and 40 ml. of ethanol and a mixture of 40 ml. of acetic acid and 40 ml. of water was added. The reaction mixture was stirred at 40° C. for 4 hours. The reaction mixture was then made basic to pH 9 with sodium hydroxide solution and extracted with diethyl ether, ethyl acetate and methylene chloride. The three organic extracts were combined, treated with charcoal, dried over anhydrous magnesium sulfate and concentrated at reduced pressure to obtain a yellow solid which was recrystallized from ethanol to obtain the product as a yellow green solid, m.p. 162°–163° C.

EXAMPLE 11

7-(4'-Chlorophenyl)-6-methyl-1,6-naphthyridine-5-(6H)-one

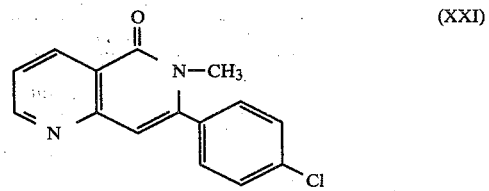

(XXI)

5 ml. of trifluromethanesulfonic acid were added to 4.6 g. (16.0 mmol.) of 2-(4'-chlorobenzoylmethyl)nicotinic acid N-methylamide (Compound XX) in 30 ml. chloroform stirred at 0° C. The resulting reaction mixture was then stirred at room temperature for 3 hours, chilled to 0° C. and made basic with 10% sodium hydroxide solution. Celite and charcoal were added and the entire reaction mixture was filtered through Celite. The phases were separated and the aqueous phase was extracted with methylene chloride. The organic phase and the methylene chloride extract were combined, dried over anhydrous magnesium sulfate and concentrated at reduced pressure to give the crude product as a light brown solid. The crude product was recrystallized from methylene chloride/diethyl ether and then from ethanol to give the product (2.5 g.), m.p. 139°–140° C.

| Test A: | $ED_{50}$ = 134 mg./kg. i.p. |
|---|---|
| | 32% 200 mg./kg. p.o. |

The compound of this example may be converted into its pharmaceutically acceptable acid addition salts by conventional means.

EXAMPLES 12–17

The following hydroxylactams of Formula VII may be synthesized from the corresponding compounds of Formulae V and VI by the process of Examples 3 and 5:

| | $R_1$ | $R_2$ | $R_3$ | $R_4$ | |
|---|---|---|---|---|---|
| Example 12 | —CH₃ | 3-CF₃ | H | H | m.p. 139° C. |
| Example 13 | —CH₃ | 3-OCH₃ | 4-OCH₃ | H | m.p. 157° C. |
| Example 14 | —CH₃ | H | H | H | m.p. 141° C. (dec.) |
| Example 15 | —CH₃ | 2-OCH₃ | H | H | |
| Example 16 | —CH₃ | 2-F | H | H | |
| Example 17 | —CH₃ | 2-F | 6-F | H | |

EXAMPLES 18–19

The following enamines of Formula X may be synthesized from the corresponding compounds of Formula V and IX by the process of Example 9:

| | $R_1$ | $R_2$ | $R_3$ | $R_4$ | |
|---|---|---|---|---|---|
| Example 18 | —CH₃ | H | H | H | m.p. 159°–161° C. |
| Example 19 | —CH₃ | 4-CH₃ | H | H | m.p. 88°–116° C. (crude) |

EXAMPLES 20-22A

The following ketones of Formula VIII may be synthesized from the compounds of Formulae V and VI by the process of Example 7 or from the compounds of Formula X by the process of Example 10:

|  | $R_1$ | $R_2$ | $R_3$ | $R_4$ |  |
|---|---|---|---|---|---|
| Example 20 | —$CH_3$ | 4-$CH_3$ | H | H | m.p. 120°-134° C. (crude) |
| Example 21 | —$CH_3$ | 3-Cl | H | H | m.p. 200°-206° C. |
| Example 22 | —$C_2H_5$ | 2-Cl | H | H |  |
| Example 22A | —$CH_3$ | 4-N-$(CH_3)_2$ | H | H | m.p. 173° C. |

EXAMPLES 23-41

The following compounds of Formula I may be prepared by the processes of the preceding examples:

|  | $R_1$ | $R_2$ | $R_3$ | $R_4$ |  |
|---|---|---|---|---|---|
| Example 23 | —$CH_3$ | 3-$OCH_3$ | 4-$OCH_3$ | H | m.p. 136°-137° C. |
| Example 24 | —$CH_3$ | H | H | H | m.p. 90°-90.5° C. |
| Example 25 | —$CH_3$ | 4-$CH_3$ | H | H | m.p. 134° C. |
| Example 26 | —$CH_3$ | 3-Cl | H | H | m.p. 143° C. |
| Example 27 | —$CH_3$ | 3-$CF_3$ | H | H | m.p. 135° C. |
| Example 28 | —$CH_3$ | 2-$OCH_3$ | H | H | m.p. 154° C. |
| Example 29 | —$CH_3$ | 2-F | H | H | m.p. 121°-123° C. |
| Example 30 | —$CH_3$ | 2-F | 6-F | H | m.p. 162°-163° C. |
| Example 31 | —$C_2H_5$ | 2-Cl | H | H |  |
| Example 32 | i-$C_3H_7$ | 2-$CH_3$ | H | H |  |
| Example 33 | i-$C_3H_7$ | 2-Cl | H | H |  |
| Example 34 | n-$C_4H_9$ | 2-$CH_3$ | H | H |  |
| Example 35 | —$C_2H_5$ | 2-$CH_3$ | H | H |  |
| Example 36 | —$CH_3$ | 2-Br | H | H |  |
| Example 37 | —$CH_3$ | 2-$CH_3$ | 4-$CH_3$ | 6-$CH_3$ |  |
| Example 38 | —$CH_3$ | 2-Cl | 6-Cl | H |  |
| Example 39 | —$CH_3$ | 2-$SCH_3$ | H | H | m.p. 153°-155° C. |
| Example 40 | —$CH_3$ | 2-N—$(CH_3)_2$ | H | H | m.p. 135°-136° C. |
| Example 41 | —$CH_3$ | 4-N—$(CH_3)_2$ | H | H | m.p. 199° C. |

The compounds of these examples may be converted into their pharmaceutically acceptable acid addition salts by conventional means.

What is claimed is:

1. A compound of the formula

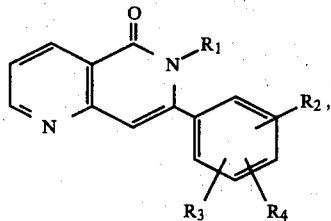

or a pharmaceutically acceptable acid addition salt thereof,
wherein
$R_1$ is $C_{1-4}$alkyl,
$R_2$ is hydrogen, $C_{1-4}$alkyl, halo, trifluoromethyl, $C_{1-4}$alkylthio or -$NR_5R_6$, wherein each of $R_5$ and $R_6$ is independently hydrogen or $C_{1-3}$alkyl,
$R_3$ is hydrogen, $C_{1-3}$alkyl, halo or trifluoromethyl, and
$R_4$ is hydrogen, $C_{1-3}$alkyl or halo,
wherein each halo is independently fluoro, chloro or bromo.

2. A compound according to claim 1 in free base form.

3. A compound according to claim 1, or a pharmaceutically acceptable acid addition salt thereof, wherein
$R_1$ is $C_{1-3}$alkyl,
$R_2$ is hydrogen, $C_{1-2}$alkyl, chloro, fluoro or 2- or 3-dimethylamino,
$R_3$ is hydrogen, $C_{1-2}$alkyl, chloro or fluoro, and
$R_4$ is hydrogen, with the proviso that at least one of the ortho positions of the phenyl ring has a hydrogen atom or a fluoro substituent.

4. A compound according to claim 3 in free base form.

5. A compound according to claim 3, or a pharmaceutically acceptable acid addition salt thereof, wherein
$R_1$ is $C_{1-2}$alkyl,
$R_2$ is $C_{1-2}$alkyl, chloro, fluoro or 3-dimethylamino, and
$R_3$ is hydrogen.

6. A compound according to claim 5 in free base form.

7. A compound according to claim 5, or a pharmaceutically acceptable acid addition salt thereof, wherein $R_1$ is methyl.

8. A compound according to claim 7 in free base form.

9. A compound according to claim 5, or a pharmaceutically acceptable acid addition salt thereof, wherein $R_2$ is 2-$C_{1-2}$alkyl, 2-chloro, 2-fluoro or 3-dimethylamino.

10. A compound according to claim 9 in free base form.

11. A compound according to claim 9, or a pharmaceutically acceptable acid addition salt thereof, wherein $R_1$ is methyl.

12. A compound according to claim 11 in free base form.

13. The compound according to claim 12 having the formula

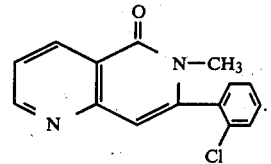

14. The compound according to claim 12 having the formula

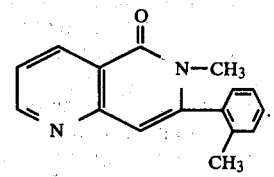

15. The compound according to claim 12 having the formula

16. The compound according to claim 8 having the formula

[structure: pyridine-fused lactam with N—CH3 and 3-(N(CH3)2)phenyl substituent]

[structure: pyridine-fused lactam with N—CH3 and 4-Cl-phenyl substituent]

17. A pharmaceutical composition comprising an effective amount of a compound according to claim 1, or a pharmaceutically acceptable acid addition salt thereof, and a pharmaceutically acceptable carrier, said effective amount being an amount effective for muscle relaxation or for the treatment of inflammation.

18. A pharmaceutical composition according to claim 17 in unit dosage form.

19. A pharmaceutical composition according to claim 17 wherein said compound is

[structure: pyridine-fused lactam with N—CH3 and 2-Cl-phenyl substituent]

20. A pharmaceutical composition according to claim 17 wherein said compound is

[structure: pyridine-fused lactam with N—CH3 and 2-CH3-phenyl substituent]

21. A method of treating muscle spasms comprising administering to a mammal in need of said treatment a muscle relaxant effective amount of a compound of the formula

[structure with $R_1$, $R_2$, $R_3$, $R_4$ substituents]

or a pharmaceutically acceptable acid addition salt thereof,
wherein
$R_1$ is $C_{1-4}$alkyl,
$R_2$ is hydrogen, $C_{1-4}$alkyl, $C_{1-4}$alkoxy, halo, trifluoromethyl, $C_{1-4}$alkylthio or -$NR_5R_6$, wherein each of $R_5$ and $R_6$ is independently hydrogen or $C_{1-3}$alkyl,
$R_3$ is hydrogen, $C_{1-3}$alkyl, $C_{1-3}$alkoxy, halo or trifluoromethyl, and
$R_4$ is hydrogen, $C_{1-3}$alkyl, $C_{1-3}$alkoxy or halo, with the proviso that at least one of $R_3$ and $R_4$ is other than hydrogen when $R_2$ is 4-$NR_5R_6$,
wherein each halo is independently fluoro, chloro or bromo.

22. A method of treating inflammation comprising administering to a mammal in need of said treatment an anti-inflammatory effective amount of a compound of the formula

[structure with $R_1$, $R_2$, $R_3$, $R_4$ substituents]

or a pharmaceutically acceptable acid addition salt thereof,
wherein
$R_1$ is $C_{1-4}$alkyl,
$R_2$ is hydrogen, $C_{1-4}$alkyl, $C_{1-4}$alkoxy, halo, trifluoromethyl, $C_{1-4}$alkylthio or -$NR_5R_6$, wherein each of $R_5$ and $R_6$ is independently hydrogen or $C_{1-3}$alkyl,
$R_3$ is hydrogen, $C_{1-3}$alkyl, $C_{1-3}$alkoxy, halo or trifluoromethyl, and
$R_4$ is hydrogen, $C_{1-3}$alkyl, $C_{1-3}$alkoxy or halo,
wherein each halo is independently fluoro, chloro or bromo.

23. A method according to claim 21 wherein said compound is the compound of the formula

[structure: pyridine-fused lactam with N—CH3 and 2-Cl-phenyl substituent]

24. A method according to claim 21 wherein said compound is the compound of the formula 25. A method according to claim 22 wherein said compound is the compound of the formula
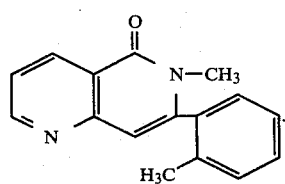
26. A compound according to claim 1, or a pharmaceutically acceptable acid addition salt thereof, wherein when $R_2$ is $-NR_5R_6$, it is in an ortho or meta position.
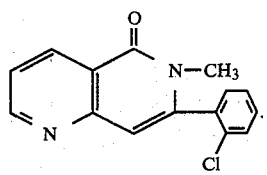
* * * * *